United States Patent [19]
Hawley et al.

[11] Patent Number: 5,962,644
[45] Date of Patent: Oct. 5, 1999

[54] PORCINE CD34

[75] Inventors: Robert J. Hawley, Newton; Rodney L. Monroy, Rockport, both of Mass.

[73] Assignee: BioTransplant, Inc., Charlestown, Mass.

[21] Appl. No.: 08/475,634

[22] Filed: Jun. 7, 1995

[51] Int. Cl.⁶ .......................... C07K 14/435; C07K 14/47
[52] U.S. Cl. ............................................ 530/350; 530/395
[58] Field of Search ...................................... 530/350, 395, 530/806, 829

[56] References Cited

PUBLICATIONS

Simmons, D. L. et al. J. Immunol. 148: 267–271, Jan. 1992.
Titley, I. et al. Leukocyte Typing V, Proceedings of the Fifth International Workshop and Conference Held in Boston Nov. 3–7, 1993, Schlossman et al., Eds., Oxford University Press, New York, NY, vol. 1, pp. 858–861, 1995.

Krause, D. et al. Blood 84: 691–701, Aug. 1994.

Greaves, M. F. et al. Leukocyte Typing V, Proceedings of the Fifth International Workshop and Conference Held in Boston Nov. 3–7 1993, Schlossman et al., Eds, Oxford University Press, New York, NY, vol. 1, pp. 840–846, 1995.

Fina, L. et al. Blood 75 (12): 2417–2426, Jun. 1990.

*Primary Examiner*—Christina Y. Chan
*Assistant Examiner*—Phillip Gambel
*Attorney, Agent, or Firm*—Elliot M. Olstein; Raina Semionow

[57] ABSTRACT

Porcine CD34, oligonucleotides encoding the porcine CD34, porcine CD34 antibodies and methods of making and using each are disclosed.

17 Claims, 3 Drawing Sheets

FIGURE 1A

```
                                        ATCTATCTCT TCGGAAGCGG CGCGGGAAGG    30

ATG CTG ATC CGC AGG GGC GCG CGC GCG GGG CGC GGG ATG CCG CGG GGC             78
Met Leu Ile Arg Arg Gly Ala Arg Ala Gly Arg Gly Met Pro Arg Gly
    -30                 -25                 -20

TGG ACC ACG CTC TGC TTG CTG AGT TTG CTG CCC TCT GGG TTC ACA GCT            126
Trp Thr Thr Leu Cys Leu Leu Ser Leu Leu Pro Ser Gly Phe Thr Ala
-15                 -10                  -5                   1

GTG AAC AGC TCA ACT ATT GCT TCC ACC TTG CCA GCT GCC GCT GGG TCA            174
Val Asn Ser Ser Thr Ile Ala Ser Thr Leu Pro Ala Ala Ala Gly Ser
                5                  10                  15

ACT CCC ACC GGG CCG GCT ACC GCA GGG GCA GCT ATC ACC GGG TCA ACT            222
Thr Pro Thr Gly Pro Ala Thr Ala Gly Ala Ala Ile Thr Gly Ser Thr
               20                  25                  30

ATC TCA GAC ATA TCT TCA CCT GTT TCT ACA AAT ATA TCC AAC GAG GAA            270
Ile Ser Asp Ile Ser Ser Pro Val Ser Thr Asn Ile Ser Asn Glu Glu
               35                  40                  45

ACC ACA TCA GAT GCT TTC GAA AGT GCC AGC CTC CAC ACT GTC TCT CAG            318
Thr Thr Ser Asp Ala Phe Glu Ser Ala Ser Leu His Thr Val Ser Gln
50                  55                  60                  65

GGC AGC AGT GGG ACC ACC GTA GCC ATC TCA GGC CCT ACA GTT AAT TTC            366
Gly Ser Ser Gly Thr Thr Val Ala Ile Ser Gly Pro Thr Val Asn Phe
               70                  75                  80

ATG TCT ACC TCG GCG GTC ACC CTC GTC CCC GAA ACC GTT AAC TCT TCT            414
Met Ser Thr Ser Ala Val Thr Leu Val Pro Glu Thr Val Asn Ser Ser
               85                  90                  95

GTC CAG CCT CAG ACC TCT CTA GCC ACA GCG TCC TCC GCC ACC ATC AAC            462
Val Gln Pro Gln Thr Ser Leu Ala Thr Ala Ser Ser Ala Thr Ile Asn
              100                 105                 110

TTT ACA ACT TCA GAG GTG ACC CTG CAG CCC AGC ACG TTC CCA GGA AAT            510
Phe Thr Thr Ser Glu Val Thr Leu Gln Pro Ser Thr Phe Pro Gly Asn
              115                 120                 125
```

FIGURE 1B

```
GTT TCA GAC CCC CTC TAC AAC AGT ACC AGC CCT GCG AGA TCC CCC ACC    558
Val Ser Asp Pro Leu Tyr Asn Ser Thr Ser Pro Ala Arg Ser Pro Thr
130             135             140             145

AGC CCC TAC ACA TCA TCT CCT CCT ACC CCA GGT AGC CAC AAG GGG GAA    606
Ser Pro Tyr Thr Ser Ser Pro Pro Thr Pro Gly Ser His Lys Gly Glu
                150             155             160

GTC AAA TGT GCC CAA ATC AAA GAG GTG AAA TTG ACC CAA GGT ATC TGC    654
Val Lys Cys Ala Gln Ile Lys Glu Val Lys Leu Thr Gln Gly Ile Cys
            165             170             175

CTG GAG CGA AAT GAG ACC TCC GGC TGC GAG AAG TTT AAG AAG GAC AAT    702
Leu Glu Arg Asn Glu Thr Ser Gly Cys Glu Lys Phe Lys Lys Asp Asn
        180             185             190

GGA GAG AAG TTG ATG CAA ATC CTG TGT GGG CAG GAG CAG GCT GAG GCC    750
Gly Glu Lys Leu Met Gln Ile Leu Cys Gly Gln Glu Gln Ala Glu Ala
    195             200             205

GGG CCA GGG GTG TGC TCC TTG CTC CTT GCC CAA TCT GAG GTG AAA CCT    798
Gly Pro Gly Val Cys Ser Leu Leu Leu Ala Gln Ser Glu Val Lys Pro
210             215             220             225

CAC TGC CTG CTG CTG GTC TTG GCC AAC GGA ACA GAA CTT AGC AGC AAG    846
His Cys Leu Leu Leu Val Leu Ala Asn Gly Thr Glu Leu Ser Ser Lys
                230             235             240

TTC CTG CTT CTG GAA AAG CAC CAG TCT GAA CTG AGA GAG ATG AGC ATC    894
Phe Leu Leu Leu Glu Lys His Gln Ser Glu Leu Arg Glu Met Ser Ile
            245             250             255

CAA AAC TTC TCG AAA CAA GAT GTT AGG AGC CAC CAG AGC TAC TCC CGA    942
Gln Asn Phe Ser Lys Gln Asp Val Arg Ser His Gln Ser Tyr Ser Arg
        260             265             270

AAG ACC TTG ATT GCA CTG GTC ACC TCG GGG ATC CTG CTG GCT GTC TTG    990
Lys Thr Leu Ile Ala Leu Val Thr Ser Gly Ile Leu Leu Ala Val Leu
    275             280             285
```

FIGURE 1C

```
GGC ATC ACT GGC TAC TTG CTG ATG AAC CGT CGC AGT TGG AGC CCT ACA  1038
Gly Ile Thr Gly Tyr Leu Leu Met Asn Arg Arg Ser Trp Ser Pro Thr
290             295             300             305

GGA GAA AGG CTG GAG CTG GAA CCC TGA                               1065
Gly Glu Arg Leu Glu Leu Glu Pro TER
            310
```

PORCINE CD34

This invention relates to the field of antibodies that are specific to cell surface antigens and more particularly to such antibodies and compositions and methods that are useful for recovering porcine hematopoietic progenitor cells; in particular, stem cells. The invention further relates to isolated porcine cells which are recognized by an antibody of the invention and to the use of such porcine cells.

Organ procurement currently poses one of the major problems in organ transplantation, as the number of patients requiring transplants far exceeds the number of organs available. Despite some promising results with non-human primate-to-human xenotransplantation studies, it is very unlikely that, in the future, there will be widespread use of non-human primate organs. Firstly, chimpanzees and baboons are endangered species and there is much societal opposition to the use of such animals for experimental purposes. Secondly, there is concern over the transmission of non-human primate diseases when organs from such species are used in human transplants. It has been recognized that the use of swine organs for xenogeneic transplantation is an attractive alternative source for organs. There is a close similarity between swine and humans with regards to parameters relevant to transplantation, including renal, cardiovascular and pulmonary physiology (Tumbleson, *Swine in Biomedical Research,* New York Plenum Press, 1986). Pigs are frequently sacrificed for human consumption; most swine diseases are unlikely to cause serious problems to humans and pigs are relatively easy to breed. Specifically, the organs of miniature swine seem appropriate for use as xenografts. While the weight of domestic swine are frequently in excess of 1,000 lb., the weight of the miniature swine is compatible with the weight of many adults, approximately 200 lb.

The second major problem regarding current transplantation procedures is the need for chronic immunosuppression in order to maintain the transplanted organ. The prolonged use of immunosuppressive agents, such as cyclosporin A, leads to renal dysfunction and may lead to graft failure. Much effort continues to be expended on means to induce immunologic tolerance which would obviate the necessity for chronic use of immunosuppression agents.

Tolerance to self major histocompatibility (MHC) antigens occurs during T cell maturation in the thymus (McDuffie et al., *J. Immunol.,* 141:1840, 1988). Exposure of the immune system to MHC antigens during ontogeny can cause the immune system to become tolerant to those antigens (Billingham, et al., *Nature* 172:603, 1953). Tolerance across major histocompatibility antigens has been achieved through the development of mixed bone marrow chimeras. It is desirable that the bone marrow population to be administered be enriched for the hematopoietic stem cells, since it is considered that it is this source of cells which will lead to prolonged bone marrow chimerism.

The development of monoclonal antibodies (mABs) to antigenic determinants on human hematopoietic cells has allowed identification and purification of subsets of marrow that contain precursor cells. Antibodies to CD34 antigen have been of interest because they react with a minor subset of cells that contains virtually all of the precursors of colony forming cells that can be detected in long-term marrow cultures. The CD34+ population of progenitor cells have been presumed to contain candidate stem cells. Indeed, populations enriched for CD34+ cells can engraft lethally irradiated baboons (Berenson et al., *J. Clin. Invest.,* 81:951, 1988).

Much has been learned in the past few years regarding the molecular biology of CD34 (Sutherland and Keating, *J. Hematotherapy,* 1:115–129, 1992). Both the human and murine cDNA genes have been cloned and sequenced. Genomic clones has been isolated and have demonstrated that both the human and murine genes are approximately 28 kb long. The human CD34 cDNA sequence predicts a molecule of 40 kDA with a maximum of nine potential N-linked glycosylation sites. The native molecule is predicted to contain a considerable number of O-linked glycans. In fact, over 35% of the 145 amino acids in the amino-terminal domain are either serine or threonine residues. The cluster of O-linked glycans in this domain may induce an extended structure to the molecule. Between the amino-terminal domain of potential heavy glycosylation and the transmembrane domain is a cysteine-rich region of 66 amino acids, which probably exhibits a globular conformation. The cytoplasmic domain of 73 amino acids contains several potential phosphorylation sites for a variety of protein kinases. The murine CD34 cDNA gene was isolated, using a probe corresponding to the human sequence, by using low stringency hybridization conditions. Both the murine and human cDNA sequences have significant homologies. The intracellular domains are >90% identical, the transmembrane and proximal extracellular domains and the cysteine-rich region are also very similar (>75% and >70% identical, respectively). The amino-terminal domains of about 145 amino acids are only 45% sequence identical.

In accordance with one aspect of the present invention there is provided an antibody against porcine CD34 antigen.

In accordance with another aspect there is provided an antibody which can be used for recovery of CD34$^+$ porcine cells.

In accordance with another aspect of the invention, there is provided a process for recovering CD34$^+$ porcine cells, preferably from porcine bone marrow.

In accordance with another aspect of the present invention, there is provided a population of CD34$^+$ porcine cells, in particular recovered from swine bone marrow or swine cord blood, preferably swine bone marrow.

In accordance with still a further aspect of the present invention, there is provided at least one polypeptide which can be used to produce an antibody which recognizes CD34$^+$ positive porcine cells and a polynucleotide encoding such polypeptide.

In accordance with yet a further aspect of the invention, porcine CD34$^+$ positive cells are employed to treat a host in particular a human patient who is to receive a porcine graft.

The porcine CD34$^+$ cells are particularly employed to produce bone marrow mixed chimerism in a human patient to aid in acceptance of a porcine graft.

BRIEF DESCRIPTION OF THE FIGURE

FIG. 1 provides the cDNA sequence of clone 1Ax2-3 (SEQ ID NO: 18) and the deduced polypeptide sequence encoded by the DNA of clone 1Ax2-3 (SEQ ID NO: 19).

Antibodies against porcine CD34$^+$ cells may be produced by use of a polypeptide of the invention or a peptide fragment thereof, which fragment includes at least one porcine CD34$^+$ epitope.

Thus, for example, the antigen may be a soluble polypeptide which is at least 95% identical to the soluble portion of the porcine CD34$^+$ antigen or may be a fragment of such polypeptide which fragment alone or in admixture with an appropriate protein is capable of generating antibodies against CD34$^+$ cells.

In this respect, in accordance with an aspect of the present invention there is provided a polypeptide which is at least 95% identical to the mature polypeptide (polypeptide without the signal or leader sequence and including the transmembrane portion) and/or to the polypeptide with the signal or leader sequence which is encoded by the DNA included in ATCC Deposit No. 97,143, 97,144 or 97,145, filed on May 12, 1995.

The cDNA of clone 1Ax2-3 (ATCC 97,143) and the deduced polypeptide sequence encoded by such DNA of clone 1Ax2-3 is shown in FIG. 1. The deduced polypeptide sequence encoded by the DNA in each of clones 1Bx2-4 and 1Cx2-5 is provided by reference to Table 1 and FIG. 1.

TABLE 1

| Changes from sequence of 1Ax2-3 | | |
|---|---|---|
| 1Bx2-4 NA POS | Substitute | Amino Acid Change |
| 202 | A for G | ALA --> THR |
| 405 | G for T | No Change |
| 596 | G for A | HIS --> ARG |
| 709 | G for A | LYS --> GLU |
| 812 | C for T | LEU --> PRO |
| 1Cx2-5 NA POS | Substitute | Amino Acid Change |
| 202 | A for G | ALA --> THR |
| 405 | G for T | No Change |
| 597 | C for T | No Change |
| 831 | G for A | THR --> ALA |

In accordance with a further aspect of the present invention, there is provided a polypeptide which is at least 95% identical to the soluble portion of the polypeptide encoded by the DNA in the deposited clones (the soluble portion is the encoded polypeptide without the leader or signal portion and without the transmembrane portion).

The present invention further relates to a peptide fragment of such above polypeptides which peptide fragment includes an epitope which produces an antibody which recognizes porcine CD34+ cells.

The present invention further relates to polynucleotides which encode polypeptides which are at least 95% identical to the polypeptide having the deduced amino acid sequence of FIG. 1 which includes amino acids 1 to 313, or amino acids −31 to 313 or amino acids 1 to 275, or amino acids −31 to 275, or to fragments of such polypeptides which fragments include at least one epitope of porcine CD34+ antigen.

As hereinabove indicated the polypeptides and peptide fragments of the present invention are employed to produce antibodies which recognize CD34+ porcine cells. Such antibodies may be produced by use of a recombinant cell which expresses a polypeptide of the present invention which includes the transmembrane portion, whereby the recombinant cell includes such polypeptide on the surface thereof. Such recombinant cell may be employed for producing an antibody which recognizes CD34+ cells by procedures known in the art; for example as described in Example 3.

Alternatively, the soluble portion of the polypeptides of the present invention may be produced by recombinant techniques and such soluble polypeptide can be used for producing an antibody which recognizes porcine CD34+ cells by procedures known in the art; e.g., as described in Example 2.

In accordance with a further embodiment, a peptide fragment of the polypeptides of the present invention, for example, one which is chemically synthesized may be combined with a suitable protein, with such combination then being employed as an immunogen for producing antibodies which recognize porcine CD34+ cells. Thus, for example, the following peptides which are from regions of the polypeptide encoded by the DNA contained in clone 1Ax2-3 which regions form disulfide bonded loops may be used in preparing an immunogen for producing an antibody which recognizes porcine CD34+ cells:

Peptide 1: Glu Val Lys Cys Ala Gln Ile Lys Glu Val Lys Leu Ile
  Gln Gly Ile Cys         (SEQ ID NO: 1)

Peptide 2: Ile Ser Gly Cys Glu Lys Phe Lys Lys Asp Asn Gly Glu
  Lys Leu Met Gln Ile Leu Cys         (SEQ ID NO: 2)

The antibodies of the present invention may be employed for recovering porcine CD34+ cells from porcine bone marrow by procedures similar to those employed for recovering CD34+ cells from human bone marrow. Thus, for example, the antibodies may be supported on a suitable support by procedures known in the art for such purpose. The antibodies may be physically supported, for example, by adsorption or through an appropriate chemical linkage. The antibodies may be supported, for example, by direct binding to a resin, such as Affigel 10 or 15, and the resulting affinity matrix used for purification of CD34+ cells. Thus, the antibodies of the present invention may be used in a column (an affinity column) to separate porcine CD34+ cells from porcine bone marrow.

The swine CD34+ cells may be used to produce mixed chimerism for inducing tolerance to an organ or tissue which is to be transplanted from swine into another species; in particular, a human. The published PCT application corresponding to PCT Application U.S. 93/00184 describes such a procedure using swine bone marrow and the porcine CD34+ cells of the present invention may be used in place of the swine bone marrow.

Published PCT Application corresponding to U.S. 94/12522 describes recovery of stem cells from swine cord blood, and the antibodies of the present invention are suitable for use in such a procedure.

Th antibodies may also be employed in an assay for determining the presence of porcine CD34+ cells using known assay procedures. For example, the antibody may be employed to determine whether or not mixed chimerism has occurred by assaying for the presence of porcine CD34+ cells in a host who has received such cells.

Thus, for example, such an assay may be effected by one of a variety of assay techniques generally referred to as immunoassays to detect the presence of porcine CD34+ cells.

Thus, in accordance with the present invention, there is provided one or more antibodies which are antibodies against one or more of the polypeptides encoded by DNA of one or more of the deposited clones. Such antibodies may be used to isolate porcine cells and in particular porcine cells from porcine bone marrow. The present invention further relates to porcine cells which are recognized by one or more of such antibodies. Such porcine cells are enriched for porcine hematopoietic progenitor cells and in particular stem cells.

The isolated porcine cells which are recognized by the antibodies of the present invention are referred to as porcine CD34+ cells in that the polypeptides of the present invention are believed to have at least a 95% identity to the porcine CD34+ antigen.

Accordingly, the present invention provides an antibody (or fragment or derivative thereof) and preferably, an antibody (or fragment or derivative thereof) which binds to porcine CD34$^+$ cells, particularly to porcine CD34$^+$ hematopoietic progenitor cells, e.g. stem cells.

The antibodies of the present invention have the characteristics of binding to an epitope of porcine CD34 antigen (e.g. CD34 positive porcine hematopoietic progenitor cells).

In accordance with another aspect of the present invention there is provided a method of preventing and/or inhibiting an immune response in human patients to a swine graft by treating the human recipient with CD34$^+$ porcine cells.

Another aspect of the invention provides a method of inhibiting an immunogenic response in a xenogeneic transplantation host, such as a human recipient, to a porcine organ or porcine tissue by introducing a porcine CD34$^+$ enriched cell population to the intended recipient prior to introduction of the porcine transplant organ or tissue.

The antibodies of the invention can be, for example, polyclonal, monoclonal, chimeric, humanized or single chain antibodies, or Fab fragments. Various procedures known in the art may be used for the production of polyclonal antibodies. For preparation of monoclonal antibodies, any technique which provides antibodies produced by continuous cell line cultures can be used. Examples include the hybridoma technique (Kohler and Milstein, 1975, Nature 256:495–497). Techniques described for the production of single-chain antibodies (U.S. Pat. No. 4,946,778) can be adapted to produce porcine CD34-specific single-chain antibodies.

The antibody against CD34$^+$ porcine cells is preferably a murine antibody; however, the antibody may be produced in other species; e.g., rat or bovine.

One aspect of the present invention provides isolated nucleic acid molecules encoding polypeptides which produce antibodies against porcine CD34$^+$ cells (including mRNAs, DNAs, cDNAs, genomic DNAs) as well as analogs and fragments thereof which produce polypeptides capable of generating such antibodies.

Another aspect of the invention provides porcine CD34$^+$ cells that preferentially enhance the development of mixed bone marrow chimerism between porcine bone marrow cells and bone marrow cells of other species in particular a primate, and to DNA sequences encoding polypeptides which can be used to produce antibodies which will specifically recognize the porcine CD34 antigen.

FIG. 1 shows the nucleic acid sequence and deduced amino acid sequence of a polynucleotide and polypeptide of the present invention. The mature polypeptide (without signal sequence) begins at amino acid 1. The transmembrane portion of the polypeptide is putatively identified as beginning at amino acid 276.

The term "isolated" means that the material is removed from its original environment (e.g., the natural environment if it is naturally occurring). For example, a naturally-occurring polynucleotide or DNA present in a living animal is not isolated, but the same polynucleotide or DNA, separated from some or all of the coexisting materials in the natural system, is isolated. Such DNA could be part of a vector and/or such polynucleotide could be part of a composition, and still be isolated in that such vector or polynucleotide is not part of its natural environment.

It is also advantageous that the sequences be in "purified" form. The term "purified" does not require absolute purity; rather, it is intended as a relative definition. The cDNA clones are obtained via manipulation of a partially purified naturally occurring substance (messenger RNA). By conversion of mRNA into a cDNA library, pure individual cDNA clones can be isolated from the synthetic library by clonal selection. Thus, creating a cDNA library from RNA and subsequently isolating individual clones from that library results in an approximately $10^6$ fold purification of the native message. Purification of starting material or natural material to at least one order of magnitude, preferably two or three orders, and more preferably four or five orders of magnitude is expressly contemplated. Furthermore, claimed polynucleotide which has a purity of preferably 0.001%, or at least 0.01% or 0.1%; and even desirably 1% by weight or greater is expressly contemplated.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the polypeptides may be identical to the coding sequences specifically described or that of the deposited clone or may be a different coding sequence which coding sequence, as a result of the redundancy or degeneracy of the genetic code, encodes the same polypeptides as the described DNA or the deposited cDNA.

The polynucleotides which encode for the polypeptide of the invention include, but are not limited to: only the coding sequence for the mature polypeptide; the coding sequence for the mature polypeptide and additional coding sequence such as a leader or secretory sequence; the coding sequence for the mature polypeptide (and optionally additional coding sequence) and non-coding sequence, such as introns or non-coding sequence 5' and/or 3' of the coding sequence for the mature polypeptide; the coding portion for the mature polypeptide without the transmembrane portion, etc.

The present invention further relates to variants of the hereinabove described polynucleotides which encode for fragments, analogs and derivatives of the polypeptides having the deduced amino acid sequence of the mature polypeptides of the invention. The variant of the polynucleotide may be a naturally occurring allelic variant of the polynucleotides or a non-naturally occurring variant of the polynucleotides.

Thus, the present invention includes polynucleotides encoding the same polypeptides specifically described as well as variants of such polynucleotides which variants encode for a fragment, derivative or analog of such polypeptides. Such nucleotide variants include deletion variants, substitution variants and addition or insertion variants.

As hereinabove indicated, the polynucleotides may have a coding sequence which is a naturally occurring allelic variant of the coding sequences specifically described. As known in the art, an allelic variant is an alternate form of a polynucleotide sequence which may have a substitution, deletion or addition of one or more nucleotides, which does not substantially alter the function of the encoded polypeptide.

The deposit(s) referred to herein [ATCC designations: ATCC 97143 (DNA plasmid 1AX2-3); ATCC 97144 (DNA plasmid 1BX2-4); and ATCC 97145 (DNA plasmid 1CX2-5)] will be maintained under the terms of the Budapest Treaty on the International Recognition of the Deposit of Micro-organisms for purposes of Patent Procedure. The deposits were deposited with the American Type Culture Collection, 10801 University Boulevard, Manassas, Va. 20110-2209 on May 12, 1995. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to polypeptides which have the deduced amino acid sequence of FIG. 1 or which have the amino acid sequence encoded by the deposited cDNA, as well as fragments, analogs and derivatives of such polypeptide.

The terms "derivative" and "analog" when referring to the polypeptides encoded by the deposited cDNA, means a polypeptide which retains essentially the same biological function or activity as such polypeptide, i.e., is capable of producing an antibody against porcine $CD34^+$ cells.

The polypeptides of the present invention may be recombinant polypeptides, natural polypeptides or synthetic polypeptides, preferably recombinant polypeptides.

The fragments, derivatives or analogs of the polypeptides encoded by the deposited cDNAs may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence, or (v) one in which a T helper cell epitope is fused to a $CD34^+$ fragment in order to increase immunogenicity. Such fragments, derivatives and analogs are deemed to be within the scope of those skilled in the art from the teachings herein.

The polypeptides and polynucleotides of the present invention are preferably provided in an isolated form, and preferably are purified to homogeneity.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., bacterial plasmids; baculovirus; yeast plasmids; etc. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: SV40 promoter, the CMV promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli.*

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli,* yeast cells, animal cells such as CHO, etc. The selection of an appropriate host is deemed to be within the scope of those skilled in the art from the teachings herein.

The following Examples illustrate the invention in various of its aspects without being a limitation on its scope.

EXAMPLE 1

Isolation and Sequencing of Porcine CD34 cDNA
Materials and Methods
Enrichment of porcine bone marrow cells Porcine bone marrow cells obtained from donor animals from a herd of partially inbred mini-swine were harvested from the femurs and humeri by aseptically scraping with bone currettes and flushing the cavity with Dulbecco's modified saline without calcium and magnesium containing 5% citrate-phosphate-dextrose solution (Sigma, St. Louis, Mo.) and gentamicin (20 ug/ml, Gibco, Grand Island, N.Y.). Cells were layered over Histopaque (sp. gr. 1.077, Sigma) and centrifuged at 400×g for 25 minutes. Low density cells were collected, washed, resuspended in Iscove's Modified Dulbecco's Media (IMDM, Gibco), 10% fetal bovine serum (FBS), Dnase (50 u/ml, Sigma), placed in tissue culture flasks (Costar, T150) at $5 \times 10^6$/ml and allowed to adhere for 60 minutes at 37 C., 5% $CO_2$ and 95% humidity. Nonadherent cells were loaded directly into an operating sterilized elutriator system (Beckman Instruments, Palo Alto, Calif.) and cells were subsequently separated as follows. Elutriation was performed using a Beckman JE-6B rotor system equipped with a 40 ml chamber. Rotor speed was kept constant at 2040 rpm and cells were separated by increasing the flow rates. Cells ($1–9 \times 10^9$) were loaded at a flow rate of 45 ml/min. After all the cells had entered into the chamber, media flow rate was increased to 50 ml/min and a first fraction (700 ml) was collected. A second fraction (700 ml) was collected by increasing flow to 75 ml/min. After collecting the second fraction media flow and rotor were turned off and chamber contents were harvested aseptically in a biological hood. The 75 ml/min fraction was found to be enriched for early hematopoietic progenitors (CFU-mix and BFU-e) by in vitro bone marrow culture assays.

Cells from the 75 ml/min fraction were pelleted by centrifugation and resuspended in Dulbecco's phosphate buffered saline solution with calcium and magnesium containing 1% BSA (DPBS). Cell concentration was adjusted to $10^8$/ml. CD2+lymphocytes and mature myeloid cells were depleted using 2 murine anti-porcine monoclonal antibodies, MSA-4 and 74-22-15, both have been shown to bind mature porcine lymphocytes and myeloid cells, respectively. The antibodies were added to the cells at a concentration of 7 µg each/$10^8$ cells, then incubated at 4 C. for 30 minutes. Cells were washed twice in cold DPBS and resuspended in 2 ml of DPBS. Goat anti-mouse IgG Dynabeads (M450, Dynal, Oslo, Norway) were washed and resuspended in DPBS and added to the cell suspension. The ratio of beads to cells was $4 \times 10^8$ beads to $1 \times 10^8$ cells. The cell-bead mixture was incubated for 30 minutes at 4 C., after which the pellet was gently resuspended by pipetting. The cells attached to the beads were collected using the appropriate sized magnetic particle concentrator (MPC, Dynal) and the unattached beads are collected in the supernatant. The supernatant was transferred to a second test tube and replaced in the MPC to remove any residual cells attached to beads. Cells were counted, cytospin slide preparations were made and cells were put into CFU assays to evaluate the preparation.

RNA isolation

Total RNA was isolated from $1 \times 10^7$ enriched porcine bone marrow cells using the Micro-scale Total RNA Separator Kit (Clontech, Palo Alto, Calif.) according to the manufacturer's instructions. Poly A+ RNA was isolated from the above using the PolyATract mRNA Isolation System (Promega, Madison, Wis.) according to the manufacturer's instructions.

Porcine genomic DNA preparation

Genomic DNA from miniswine peripheral blood mononuclear cells was prepared as previously described (Molecular Cloning: A Laboratory Manual, T. Maniatis et al. eds., Cold Spring Harbor Laboratories, Cold Spring Harbor, N.Y.).

Isolation of cDNA clones of the porcine CD34 gene

An overview of the process utilized to isolate the porcine CD34 cDNA gene is presented, followed by a detailed description. Briefly, clone pCRII/exon 8-#8 was generated from porcine genomic DNA using primer sequences derived from exon 8 of the human and mouse CD34 genes. Clone pCRII/exon 7-8 was generated from porcine bone marrow RNA using a human CD34 forward primer and nested porcine reverse primers derived from the sequence of pCRII/exon 8. Clone pCRII/9-13 was generated from bone marrow RNA using a human CD34 forward primer and nested porcine reverse primers derived from the sequence of pCRII/exon 7-8. Clone 4-5-6 B was derived from porcine bone marrow RNA by 5' RACE using porcine CD34 reverse primers derived from the sequence of pCRII/9-13. Finally, porcine forward and reverse primers were used to derive clones 1AX2-3, 1BX2-4 and 1CX2-5 independently from bone marrow RNA. The details of these constructions follow.

General PCR Protocol

PCR reactions were run in 100 ul of Standard Reaction Mix (1x Buffer PCR II (Perkin-Elmer, Norwalk, Conn.), 100 uM DNTP, 3 mM $MgCl_2$, 25 u/ml AmpliTaq polymerase (Perkin-Elmer)) and both forward and reverse primers at 200 nM. The hot start method, using Ampliwax Beads (Perkin-Elmer) according to the manufacturer's instructions, was utilized. Reactions were run in a System 9600 Thermocycler (Perkin-Elmer).

pCRII/exon 8-#8

Forward primer mCD34-4 (SEQ ID NO:3; 5'-GGTGAAGACCCTTATTACACGG) was derived from the sequence of exon 8 of the murine CD34 gene (Brown J. et al., 1991, International Immunology 3:175) and reverse primer hCD34-2R (SEQ ID NO: 4, 5'-CGTGTTGTCTTGCTGAATGG) was derived from the sequence of exon 8 of the human CD34 gene (Simmons D. L. et al., 1992, J. of Immunology 148:267). 100 ng of porcine genomic DNA was added. The following amplification profile was used:

1) 94 C. for 2 minutes
2) 39 cycles of:
   a) 94 C. for 45 sec
   b) T anneal for 60 sec
   c) 72 C. for 2 minutes
   where T anneal began at 55 C. and decreased 1 C. after every 3 cycles 3) 10 cycles of:
   a) 94 C. for 45 sec
   b) 42 C. for 60 sec
   c) 72 C. for 2 minutes
4) Soak at 4 C.

Reaction products were cloned into the vector pCR II (In Vitrogen, San Diego, Calif.) according to the manufacturer's instructions to created clone pCRII/exon 8-#8. The insert of the clone was sequenced using the Sequenase Sequencing Kit (USB, Cleveland, Ohio) according to the manufacturer's instructions.

pCRII/exon 7-8 cDNA was prepared from enriched porcine bone marrow cell poly A+ RNA using the 1st STRAND cDNA Synthesis Kit (Clontech) according to the manufacturer's instructions. Forward primer hCD34-4 (SEQ ID NO:5; 5'-GCAAGCCACCAGAGCTATT) and reverse primer hCD34-2R, were both derived from the human CD34 sequence. cDNA derived from 25 ng of poly A+ RNA was added and the following profile used:

1) 94 C. for 2 minutes
2) 36 cycles of:
   a) 96 C. for 2 sec
   b) T anneal for 45 sec
   c) 72 C. for 1 minute
   where T anneal begins at 60 C. and decreased 1 C. after every 3 cycles
3) Soak at 4 C.

A secondary reaction was run with 5 ul of the above primary as template. Forward primer hCD34-4 and reverse primer pCD34-4R (SEQ ID NO:5; 5'-AGTCACACTGGCTTTTCCCTGA), were derived from the sequence of clone pCRII/exon 8-#8. The reaction profile used was:

1) 94 C. for 2 minutes
2) 35 cycles of:
   a) 96 C. for 2 sec
   b) 55 C. for 45 sec
   c) 72 C. for 1 minute
3) Soak at 4 C.

Cloning and sequencing of the secondary product was performed as above.

pCRII/9-13

Porcine bone marrow cDNA, prepared above, was used as template for a primary PCR reaction Forward primer hCD34-1.1 (SEQ ID NO: 7; 5'-AGTACCCTTGGAAGTACCAGC), was derived from the sequence of human CD34, and reverse primer pCD34-5R (SEQ ID NO:8; 5'-AAGACAGCCAGCAGGATCC), was derived from the sequence of clone pCRII/exon 7-8. The following amplification profile was used:

1) 94 C. for 2 minutes
2) 35 cycles of:
   a) 96 C. for 2 sec
   b) 55 C. for 50 sec
   c) 72 C. for 1 minute
3) Soak at 4 C.

A secondary reaction was run with 5 ul of the above primary as template. Forward primer hCD34-1.1 and reverse primer pCD34-6R (SEQ ID NO: 9; 5'-GGTGACCAGTGCAATCAAGG), derived from the sequence of clone pCRII/exon 8-#8, were used. The reaction was run as above. Cloning and sequencing of the secondary product was performed as above.

4-5-6 B cDNA was prepared from oligo dT primed poly A+ RNA of progenitor-enriched porcine bone marrow using the 5' RACE System (Gibco) according to the manufacturer's instructions. Following RNase H treatment, the cDNA was phenol/chloroform extracted and purified over a Size-Sep 400 Column (Pharmacia, Piscataway, N.J.). The purified cDNA was then tailed with dCTP using terminal transferase from the 5' RACE System. A primary PCR reaction, containing tailed cDNA from approximately 40 ng of RNA, was run with the BRL anchor primer from the 5' RACE kit as forward primer and pCD-888 (SEQ ID NO: 10; 5'-GTGCAATCAAGGTCTTTCGG), derived from the sequence of clone pCRII/exon 7-8, as reverse primer. The following amplification profile was used:

1) 94 C. for 2 minutes
2) 10 cycles of:
   a) 96 C. for 2 sec
   b) 56 C. for 30 sec
   c) 72 C. for 1 minute
3) 72 C. for 5 minutes
4) Soak at 4 C.

The primary amplification reaction was purified free of primers and short amplification products over a cDNA Column (Pharmacia) according to the manufacturer's instructions. A secondary reaction contained 5 ul of the primary reaction product as template. The forward primer was MUAP (SEQ ID NO; 11; 5'-CTAGGCCACGCGTCGACTAGTAC), which overlaps the 5' RACE System anchor primer, and the reverse primer was pCD-662 (SEQ ID NO: 12; 5'-CCCACACAGGATTTGCATC), derived from the sequence of pCRII/9-13. The following amplification profile was used:

1) 94 C. for 2 minutes
2) 35 cycles of:
   a) 96 C. for 2 sec
   b) 56 C. for 30 sec
   c) 72 C. for 1 minute
3) 72 C. for 5 minutes
4) Soak at 4 C.

A tertiary amplification reaction contained 5 ul of the secondary reaction product. The forward primer was MUAP and the reverse primer pCD-604 (SEQ ID NO: 13; 5'-GAGGTCTCATTTCGCTCCAG), derived from the sequence of pCRII/9-16. A product of 700–800 bp was isolated from this reaction on a low melting temperature agarose gel and cloned into the vector pCRII as previously. The sequence of the 5' end of this clone, including the presumptive translational initiation codon and 5' untranslated sequence, was obtained as previously and by using the fmol Thermocyle Sequencing Kit (Promega) according to the manufacturer's instructions.

1AX2-3, 1BX2-4 and 1CX2-5

Three independent primary PCR reactions were run, using the same untailed cDNA prepared for isolation of clone 4-5-6 B. The forward primer was PIGS (SEQ ID NO:14; 5'-ATCTATCTCTTCGGAAGCGG), derived from the presumptive 5' untranslated region of porcine CD34 in clone 4-5-6 B. The reverse primer was pCD-974 (SEQ ID NO: 15; 5'-TTCTCCTGTAGGGCTCCAAC), derived from exon 7 sequences contained in clone pCRII/exon 7-8. The following amplification profile was used:

1) 94 C. for 2 minutes
2) 35 cycles of:
   a) 96 C. for 2 sec
   b) 56 C. for 30 sec
   c) 72 C. for 1 minute
3) 72 C. for 5 minutes
4) Soak at 4 C.

Secondary amplification reactions, for each of the three independent primary reactions, were run using 5 ul of the primary reaction as template. The forward primer was 5X (SEQ ID NO: 16; 5'-ATAGTTTAGCGGCCGCATCTATCT CTTCGG AAGCGG), which overlaps primer PIGS and adds a Not I site to the end. The reverse primer was 3X (SEQ ID NO: 17; 5'-CCTACAGGAGAAAGGCTGGAGCTG GAACCCTGAGCGGCCGCTAAACTAT). This primer, which overlaps sequences in pCD-974, contains porcine sequence through the end of exon 7 (derived from clone pCRII/exon 7-8) followed by human sequence found in the alternatively spliced form of human CD34 (Nakamura Y., et al., 1993, Experimental Hematology 21:236); it also adds a Not I site to the end. The following amplification profile was used:

1) 94 C. for 2 minutes
2) 7 cycles of:
   a) 96 C. for 2 sec
   b) 56 C. for 30 sec
   c) 72 C. for 1 minute
3) 72 C. for 5 minutes
4) Soak at 4 C.

The resulting products were cleaved with Not I and cloned into the Not I site of vector pRcCMV (InVitrogen) using standard methodology. One clone, in proper orientation relative to the CMV promoter of pRcCMV, from each independent amplification was chosen for sequencing. Sequence of at least one strand of each of the clones 1AX2-3, a1BX2-4 and 1CX2-5 was obtained by Sequenase and fmol sequencing reactions.

Results

The sequence of the CD34 insert of clone 1AX2-3 SEQ ID NO:18 is shown in FIG. 1, and is flanked by Not I cloning sites in the clone (not shown).

Nucleotides 1–20 of FIG. 1 are derived from amplification primer 5X; this sequence was originally derived from CD34 RACE clones 4-5-6 B. Nucleotides 1033–1065 are derived from amplification primer 3X. Nucleotides 1033–1050 encode the end of presumptive exon 7 of the porcine gene and were originally determined from porcine CD34+ clone pCRII/exon 7-8. Nucleotides 1051–1065, and correspondingly amino acids 310–313, may not match authentic porcine sequence.

The presumptive N-terminus of processed porcine CD34 (SEQ ID NO:19) is indicated with amino acid number 1. This assignment is made purely by homology to the known terminus of human CD34.

In two independently derived clones, there is an A nucleotide at position 202 and a G nucleotide at position 405; these differences may have arisen as in vitro artefacts in the PCR reactions used in the CD34 cloning or may result from polymorphisms within the porcine CD34 gene.

Identification of the sequence represented in FIG. 1 as porcine CD34 is made by comparison of the nucleic acid and amino acid sequences with those of human CD34. The porcine portions of the nucleic acid sequence in FIG. 1 are about 67% identical to human CD34, while the amino acid sequences are about 59% identical.

EXAMPLE 2

Generation of anti-CD34 Antibodies Using Soluble CD34 Secreted from *Pichia pastoris*

Materials and Methods

Construction of *Pichia pastoris* CD34 expression vector

A DNA fragment of the porcine CD34 cDNA sequence containing the mature coding sequence of CD34 minus the transmembrane domain is generated using PCR methodology. Primer mdr1 (5'-TGT CTA CTC GAG AAA AGA GAG GCT GAA GCT GTG AAC AGC TCA ACT ATT) (SEQ ID NO:20) contains an XhoI site at the 5' end followed by codons encoding Glu-Lys-Arg-*-Glu-Ala-Glu-Ala (SEQ ID NO:21) where * is the site of cleavage for the KEX2 protease. Following the Glu-Ala sequence are the codons for the amino terminal sequence of mature CD34. The antisense primer mdr2 (5'-ACTAGAATTCTTATCA CTT TCG GGA GTA GCT CTG) (SEQ ID NO:22) encodes the amino acids of CD34 immediately preceding the transmembrane domain, two in-frame translation termination codons and an EcoRI site. In particular, the antisense primer corresponds to the codons for amino acids 269–274 of the sequence shown in FIG. 1. The primer used produces a DNA encoding a polypeptide comprising amino acids 1–274. The PCR product generated from amplifying the CD34 insert from plasmid 1AX2-3 using primers mdr1 and mdr2 is digested with XhoI and EcoRI and purified from an agarose gel using the QIAEX Gel Extraction Kit (QIAGEN Inc. Chatsworth, Calif.). The purified fragment is ligated into vector pPIC9 (InVitrogen Inc.) that has been cleaved with XhoI and EcoRI, treated with alkaline phosphatase and purified by gel electrophoresis. One clone, pMDR6295, is confirmed to have the correct DNA sequence and is used to transform *Pichia pastoris*, according to the instructions detailed in the Pichia Expression Kit Manual of Methods (InVitrogen Corp., San Diego, Calif.). Transformants are screened for His+Mut+ phenotype due to integration into the HIS4 locus. Pichia genomic DNA is prepared by the Easy-DNA Kit protocol (InVitrogen Corp., San Diego, Calif.) and analyzed by PCR as described in the instruction manual. One clone, MDR6295, is verified to contain the CD34 insert and used to generate soluble secreted CD34 protein.

EXAMPLE 3

Generation of Monoclonal Antibodies Using Mouse L-cells Expressing Porcine CD34

Mammalian expression vector for L-cell transformation

Clone 1AX2-3, generated as described in Example 1, contains the CMV promoter for expression of the CD34 insert as well as an SV40-neo cassette for stable selection based on G418 resistance, and is therefore suitable as a mammalian expression vector.

L-cell Transformation

CHO and mouse L-cells are transformed by electroporation using methods previously published for transformation of CHO cells (J. Barsoum, 1990, DNA and Cell Biology 9:293). Briefly, $5 \times 10^6$ trypsinized cells are resuspended in 200 ul of 1XHeBS (20 mM HEPES pH 7.05, 137 mM NaCl, 5 mM KCl. 0.7 mM $Na_2HPO_4$ 6 mM dextrose) containing 50 ug of Pvu I linearized plasmid 1AX2-3 and 50 ug sheared salmon testes DNA. Electroporation is performed using a GenePulser apparatus (BioRad Laboratories, Hercules, Calif.) set at 290V and 250 uFD for CHO cells or at 240V and 250 uFD for L-cells cultured for 48–72 h prior to addition of G418 at 400 ug/ml to the culture medium. After the appearance of discrete colonies, the cells are trypsinized and replated to create single polyclonal lines for CHO and L-cell transformants.

EXAMPLE 4

Generation and Screening of Monoclonal Antibody Producing Lines

Immunization of Mice

Immunization of mice with the soluble fragment of porcine CD34 described in Example 2 is performed essentially as described (Antibodies: A Laboratory Manual, E. Harlow and D. Lane eds., Cold Spring Harbor Laboratories, Cold Spring Harbor, N.Y.). Briefly, 50 ug of protein is injected intraperitoneally into BABL/C mice in complete Freund's adjuvant. A boost is given 10–14 days after the primary immunization as above but in incomplete Freund's adjuvant. Fusions are performed 5 days following the boost.

For mouse L-cell immunizations, $10^6$ transformed cell (Example 3), rinsed and resuspended in PBS, are injected intraperitoneally into C3H×Balb C F1 hybrid mice. A boost is again given after 1–14 days, with fusions following 5 days after the boost.

Hybridoma Production

Hybridoma production followed standard protocols (Current Protocols in Immunology, eds. J. E. Coligan et al., Wiley and Sons, New York, N.Y.). Splenocytes from immunized animals are fused to SP2/0-Ag14 myeloma cells and HAT selected culture wells tested for anti-CD34 antibodies.

Screening of hybridomas

For hybridomas raised against soluble CD34 produced in Pichia, wells are first tested by ELISA for binding to the same protein. Positive wells are additionally tested by FACS analysis using a polyclonal CHO cell line expressing porcine CD34 (Example 3) or the untransformed parental line.

For hybridomas raised against transformed L-cells, culture wells are tested for antibody against transformed and untransformed CHO cells as above.

Positive clones are finally tested by FACS analysis for binding to a small proportion (1–4%) of porcine bone marrow cells.

Positive wells are frozen, subcloned and antibody produced in vivo as ascites fluid or in vitro.

Numerous modifications and variations of the present invention are possible in light of the above teachings; therefore, within the scope of the appended claims, the invention may be practiced otherwise than as particularly described.

What is claimed is:

1. An isolated polypeptide comprising a polypeptide selected from the group consisting of (a) a polypeptide comprising amino acids 1–274 of SEQ. ID No. 19 and (b) a polypeptide comprising conservative substitution variants of (a).

2. The isolated polypeptide of claim 1 wherein said polypeptide is (a).

3. The isolated polypeptide of claim 1 wherein said polypeptide is (b).

4. The isolated polypeptide of claim 3 wherein said polypeptide is a substitution variant wherein amino acid 27 is Thr, amino acid 158 is Arg, amino acid 196 is Glu and amino acid 230 is Pro.

5. The isolated polypeptide of claim 3 wherein said polypeptide is a substitution variant wherein amino acid 27 is Thr and amino acid 236 is Ala.

6. An isolated polypeptide comprising amino acids 1–313 of SEQ. ID NO. 19.

7. An isolated polypeptide comprising conservative substitution variants of a polypeptide comprising amino acids 1–313 of SEQ. ID NO. 19.

8. The isolated polypeptide of claim 7 wherein amino acid 27 is Thr, amino acid 158 is Arg, amino acid 196 is Glu and amino acid 230 is Pro.

9. The isolated polypeptide of claim 7 wherein amino acid 27 is Thr and amino acid 236 is Ala.

10. An isolated polypeptide comprising a polypeptide selected from the group consisting of (a) a polypeptide encoded by the DNA contained in ATCC Deposit No 97,143; and (b) a polypeptide comprising a conservative substitution variant of (a).

11. The isolated polypeptide of claim 10 wherein said polypeptide is (a).

12. The isolated polypeptide of claim 11 having a deleted transmembrane portion.

13. The isolated polypeptide of claim 10 wherein said polypeptide is (b).

14. The isolated polypeptide of claim 13 comprising a polypeptide encoded by the DNA contained in ATCC Deposit No. 97,144.

15. The isolated polypeptide of claim 14 having a deleted transmembrane portion.

16. The isolated polypeptide of claim 13 comprising a polypeptide encoded by the DNA contained in ATCC Deposit No. 97,145.

17. The isolated polypeptide of claim 16 having a deleted transmembrane portion.

* * * * *

SEQUENCE LISTING (1) GENERAL INFORMATION:

(iii) NUMBER OF SEQUENCES: 22

(2) INFORMATION FOR SEQ ID NO: 1:

(i) SEQUENCE CHARACTERISTICS:
       (A) LENGTH: 17 AMINO ACIDS
       (B) TYPE: AMINO ACID
       (D) TOPOLOGY:  LINEAR (iii) HYPOTHETICAL:  NO (xi) SEQUENCE DESCRIPTION:  SEQ ID NO: 1:

Glu Val Lys Cys Ala Gln Ile Lys Glu Val Lys Leu Ile Gln Gly Ile
              5                   10                  15

Cys (2) INFORMATION FOR SEQ ID NO: 2:

(i) SEQUENCE CHARACTERISTICS:
       (A) LENGTH: 20 AMINO ACIDS
       (B) TYPE: AMINO ACID
       (D) TOPOLOGY:  LINEAR (iii) HYPOTHETICAL:  NO (xi) SEQUENCE DESCRIPTION:  SEQ ID NO: 2:

Ile Ser Gly Cys Glu Lys Phe Lys Lys Asp Asn Gly Glu Lys Leu Met
              5                   10                  15

Gln Ile Leu Cys
         20

(2) INFORMATION FOR SEQ ID NO: 3:

(i) SEQUENCE CHARACTERISTICS:
       (A) LENGTH:  22 NUCLEOTIDES
       (B) TYPE:  NUCLEIC ACID
       (C) STRANDEDNESS:  SINGLE
       (D) TOPOLOGY:  LINEAR (iii) HYPOTHETICAL:  NO (iv) ANTI-SENSE: NO (xi) SEQUENCE DESCRIPTION:  SEQ ID NO: 3:

GGTGAAGACC CTTATTACAC GG                                                22

(2) INFORMATION FOR SEQ ID NO: 4:

(i) SEQUENCE CHARACTERISTICS:
       (A) LENGTH: 20 nucleotides
       (B) TYPE:  nucleic acid
       (C) STRANDEDNESS:  SINGLE
       (D) TOPOLOGY:  LINEAR (iii) HYPOTHETICAL:  NO (iv) ANTI-SENSE:  NO (xi) SEQUENCE DESCRIPTION:  SEQ ID NO: 4:

CGTGTTGTCT TGCTGAATGG                                                   20

(2) INFORMATION FOR SEQ ID NO: 5:

(i) SEQUENCE CHARACTERISTICS:

(A) LENGTH: 19 NUCLEOTIDES
            (B) TYPE: NUCLEIC ACID
            (C) STRANDEDNESS: SINGLE
            (D) TOPOLOGY: LINEAR (iii) HYPOTHETICAL: NO (iv) ANTI-SENSE: NO (xi) SEQUENCE DESCRIPTION: SEQ ID NO: 5:

GCAAGCCACC AGAGCTATT                                                    19

(2) INFORMATION FOR SEQ ID NO: 6:

(i) SEQUENCE CHARACTERISTICS:
            (A) LENGTH: 22 NUCLEOTIDES
            (B) TYPE: NUCLEIC ACID
            (C) STRANDEDNESS: SINGLE
            (D) TOPOLOGY: LINEAR (iii) HYPOTHETICAL: NO (iv) ANTI-SENSE: YES (xi) SEQUENCE DESCRIPTION: SEQ ID NO: 6:

AGTCACACTG GCTTTTCCCT GA                                                22

(2) INFORMATION FOR SEQ ID NO: 7:

(i) SEQUENCE CHARACTERISTICS:
            (A) LENGTH: 21 NUCLEOTIDES
            (B) TYPE: NUCLEIC ACID
            (C) STRANDEDNESS: DOUBLE
            (D) TOPOLOGY: LINEAR (iii) HYPOTHETICAL: NO (iv) ANTI-SENSE: NO (xi) SEQUENCE DESCRIPTION: SEQ ID NO: 7:

AGTACCCTTG GAAGTACCAG C                                                 21

(2) INFORMATION FOR SEQ ID NO: 8:

(i) SEQUENCE CHARACTERISTICS:
            (A) LENGTH: 19 NUCLEOTIDES
            (B) TYPE: NUCLEIC ACID
            (C) STRANDEDNESS: SINGLE
            (D) TOPOLOGY: LINEAR (iii) HYPOTHETICAL: NO (iv) ANTI-SENSE: NO (xi) SEQUENCE DESCRIPTION: SEQ ID NO: 8:

AAGACAGCCA GCAGGATCC                                                    19

(2) INFORMATION FOR SEQ ID NO: 9:

(i) SEQUENCE CHARACTERISTICS:
            (A) LENGTH: 20 NUCLEOTIDES
            (B) TYPE: NUCLEIC ACID
            (C) STRANDEDNESS: SINGLE
            (D) TOPOLOGY: LINEAR (iii) HYPOTHETICAL: NO (iv) ANTI-SENSE: NO (xi) SEQUENCE DESCRIPTION: SEQ ID NO: 9:

GGTGACCAGT GCAATCAAGG                                                   20

(2) INFORMATION FOR SEQ ID NO: 10:

(i) SEQUENCE CHARACTERISTICS:
        (A) LENGTH: 20 NUCLEOTIDES
        (B) TYPE: NUCLEIC ACID
        (C) STRANDEDNESS: SINGLE
        (D) TOPOLOGY: LINEAR (iii) HYPOTHETICAL: NO (iv) ANTI-SENSE: YES (xi) SEQUENCE DESCRIPTION: SEQ ID NO: 10:

GTGCAATCAA GGTCTTTCGG                                             20

(2) INFORMATION FOR SEQ ID NO: 11:

(i) SEQUENCE CHARACTERISTICS:
        (A) LENGTH: 23 NUCLEOTIDES
        (B) TYPE: NUCLEIC ACID
        (C) STRANDEDNESS: SINGLE
        (D) TOPOLOGY: LINEAR (iii) HYPOTHETICAL: NO (iv) ANTI-SENSE: NO (xi) SEQUENCE DESCRIPTION: SEQ ID NO: 11:

CTAGGCCACG CGTCGACTAG TAC                                          23

(2) INFORMATION FOR SEQ ID NO: 12:

(i) SEQUENCE CHARACTERISTICS:
        (A) LENGTH: 19 NUCLEOTIDES
        (B) TYPE: NUCLEIC ACID
        (C) STRANDEDNESS: SINGLE
        (D) TOPOLOGY: LINEAR (iii) HYPOTHETICAL: YES (iv) ANTI-SENSE: NO (xi) SEQUENCE DESCRIPTION: SEQ ID NO: 12:

CCCACACAGG ATTTGCATC                                                19

(2) INFORMATION FOR SEQ ID NO: 13:

(i) SEQUENCE CHARACTERISTICS:
        (A) LENGTH: 20 NUCLEOTIDES
        (B) TYPE: NUCLEIC ACID
        (C) STRANDEDNESS: SINGLE
        (D) TOPOLOGY: LINEAR (iii) HYPOTHETICAL: NO (iv) ANTI-SENSE: NO (xi) SEQUENCE DESCRIPTION: SEQ ID NO: 13:

GAGGTCTCAT TTCGCTCCAG                                             20

(2) INFORMATION FOR SEQ ID NO: 14:

(i) SEQUENCE CHARACTERISTICS:
        (A) LENGTH: 20 NUCLEOTIDES
        (B) TYPE: NUCLEIC ACID
        (C) STRANDEDNESS: SINGLE
        (D) TOPOLOGY: LINEAR (iii) HYPOTHETICAL: NO (iv) ANTI-SENSE: YES (xi) SEQUENCE DESCRIPTION: SEQ ID NO: 14:

ATCTATCTCT TCGGAAGCGG                                                    20

(2) INFORMATION FOR SEQ ID NO: 15:

(i) SEQUENCE CHARACTERISTICS:
         (A) LENGTH: 20 NUCLEOTIDES
         (B) TYPE: NUCLEIC ACID
         (C) STRANDEDNESS: SINGLE
         (D) TOPOLOGY: LINEAR (iii) HYPOTHETICAL: NO (iv) ANTI-SENSE: NO (xi) SEQUENCE DESCRIPTION: SEQ ID NO: 15:

TTCTCCTGTA GGGCTCCAAC                                                    20

(2) INFORMATION FOR SEQ ID NO: 16:

(i) SEQUENCE CHARACTERISTICS:
         (A) LENGTH: 36 NUCLEOTIDES
         (B) TYPE: NUCLEIC ACID
         (C) STRANDEDNESS: SINGLE
         (D) TOPOLOGY: LINEAR (iii) HYPOTHETICAL: YES (iv) ANTI-SENSE: NO (xi) SEQUENCE DESCRIPTION: SEQ ID NO: 16:

ATAGTTTAGC GGCCGCATCT ATCTCTTCGG AAGCGG                                  36

(2) INFORMATION FOR SEQ ID NO: 17:

(i) SEQUENCE CHARACTERISTICS:
         (A) LENGTH: 49 NUCLEOTIDES
         (B) TYPE: NUCLEIC ACID
         (C) STRANDEDNESS: SINGLE
         (D) TOPOLOGY: LINEAR (iii) HYPOTHETICAL: NO (iv) ANTI-SENSE: NO (xi) SEQUENCE DESCRIPTION: SEQ ID NO: 17:

CCTACAGGAG AAAGGCTGGA GCTGGAACCC TGAGCGGCCG CTAAACTAT                    49

(2) INFORMATION FOR SEQ ID NO: 18:

(i) SEQUENCE CHARACTERISTICS:
         (A) LENGTH: 1065 NUCLEOTIDES
         (B) TYPE: NUCLEIC ACID
         (C) STRANDEDNESS: SINGLE
         (D) TOPOLOGY: LINEAR (iii) HYPOTHETICAL: NO (iv) ANTI-SENSE: NO (xi) SEQUENCE DESCRIPTION: SEQ ID NO: 18:

ATCTATCTCT TCGGAAGCGG CGCGGGAAGG                                         30

ATG CTG ATC CGC AGG GGC GCG CGC GCG GGG CGC GGG ATG CCG CGG GGC          78
Met Leu Ile Arg Arg Gly Ala Arg Ala Gly Arg Gly Met Pro Arg Gly
-30             -25                 -20

TGG ACC ACG CTC TGC TTG CTG AGT TTG CTG CCC TCT GGG TTC ACA GCT         126
Trp Thr Thr Leu Cys Leu Leu Ser Leu Leu Pro Ser Gly Phe Thr Ala

-continued

| | | | | | | | | | | | | | | | | |
|---|---|---|---|---|---|---|---|---|---|---|---|---|---|---|---|---|
| -15 | | | | | -10 | | | | | -5 | | | | | 1 | |

| | | | | | | | | | | | | | | | |
|---|---|---|---|---|---|---|---|---|---|---|---|---|---|---|---|
| GTG | AAC | AGC | TCA | ACT | ATT | GCT | TCC | ACC | TTG | CCA | GCT | GCC | GCT | GGG | TCA | 174 |
| Val | Asn | Ser | Ser | Thr | Ile | Ala | Ser | Thr | Leu | Pro | Ala | Ala | Ala | Gly | Ser |
| | | | 5 | | | | | 10 | | | | | 15 | | |

| ACT | CCC | ACC | GGG | CCG | GCT | ACC | GCA | GGG | GCA | GCT | ATC | ACC | GGG | TCA | ACT | 222 |
| Thr | Pro | Thr | Gly | Pro | Ala | Thr | Ala | Gly | Ala | Ala | Ile | Thr | Gly | Ser | Thr |
| | | 20 | | | | | 25 | | | | | 30 | | | |

| ATC | TCA | GAC | ATA | TCT | TCA | CCT | GTT | TCT | ACA | AAT | ATA | TCC | AAC | GAG | GAA | 270 |
| Ile | Ser | Asp | Ile | Ser | Ser | Pro | Val | Ser | Thr | Asn | Ile | Ser | Asn | Glu | Glu |
| | 35 | | | | | 40 | | | | | 45 | | | | |

| ACC | ACA | TCA | GAT | GCT | TTC | GAA | AGT | GCC | AGC | CTC | CAC | ACT | GTC | TCT | CAG | 318 |
| Thr | Thr | Ser | Asp | Ala | Phe | Glu | Ser | Ala | Ser | Leu | His | Thr | Val | Ser | Gln |
| 50 | | | | | 55 | | | | | 60 | | | | | 65 |

| GGC | AGC | AGT | GGG | ACC | ACC | GTA | GCC | ATC | TCA | GGC | CCT | ACA | GTT | AAT | TTC | 366 |
| Gly | Ser | Ser | Gly | Thr | Thr | Val | Ala | Ile | Ser | Gly | Pro | Thr | Val | Asn | Phe |
| | | | 70 | | | | | 75 | | | | | 80 | | |

| ATG | TCT | ACC | TCG | GCG | GTC | ACC | CTC | GTC | CCC | GAA | ACC | GTT | AAC | TCT | TCT | 414 |
| Met | Ser | Thr | Ser | Ala | Val | Thr | Leu | Val | Pro | Glu | Thr | Val | Asn | Ser | Ser |
| | | 85 | | | | | 90 | | | | | 95 | | | |

| GTC | CAG | CCT | CAG | ACC | TCT | CTA | GCC | ACA | GCG | TCC | TCC | GCC | ACC | ATC | AAC | 462 |
| Val | Gln | Pro | Gln | Thr | Ser | Leu | Ala | Thr | Ala | Ser | Ser | Ala | Thr | Ile | Asn |
| | 100 | | | | | 105 | | | | | 110 | | | | |

| TTT | ACA | ACT | TCA | GAG | GTG | ACC | CTG | CAG | CCC | AGC | ACG | TTC | CCA | GGA | AAT | 510 |
| Phe | Thr | Thr | Ser | Glu | Val | Thr | Leu | Gln | Pro | Ser | Thr | Phe | Pro | Gly | Asn |
| | 115 | | | | | 120 | | | | | 125 | | | | |

| GTT | TCA | GAC | CCC | CTC | TAC | AAC | AGT | ACC | AGC | CCT | GCG | AGA | TCC | CCC | ACC | 558 |
| Val | Ser | Asp | Pro | Leu | Tyr | Asn | Ser | Thr | Ser | Pro | Ala | Arg | Ser | Pro | Thr |
| 130 | | | | | 135 | | | | | 140 | | | | | 145 |

| AGC | CCC | TAC | ACA | TCA | TCT | CCT | CCT | ACC | CCA | GGT | AGC | CAC | AAG | GGG | GAA | 606 |
| Ser | Pro | Tyr | Thr | Ser | Ser | Pro | Pro | Thr | Pro | Gly | Ser | His | Lys | Gly | Glu |
| | | | 150 | | | | | 155 | | | | | 160 | | |

| GTC | AAA | TGT | GCC | CAA | ATC | AAA | GAG | GTG | AAA | TTG | ACC | CAA | GGT | ATC | TGC | 654 |
| Val | Lys | Cys | Ala | Gln | Ile | Lys | Glu | Val | Lys | Leu | Thr | Gln | Gly | Ile | Cys |
| | | 165 | | | | | 170 | | | | | 175 | | | |

| CTG | GAG | CGA | AAT | GAG | ACC | TCC | GGC | TGC | GAG | AAG | TTT | AAG | AAG | GAC | AAT | 702 |
| Leu | Glu | Arg | Asn | Glu | Thr | Ser | Gly | Cys | Glu | Lys | Phe | Lys | Lys | Asp | Asn |
| | 180 | | | | | 185 | | | | | 190 | | | | |

| GGA | GAG | AAG | TTG | ATG | CAA | ATC | CTG | TGT | GGG | CAG | GAG | CAG | GCT | GAG | GCC | 750 |
| Gly | Glu | Lys | Leu | Met | Gln | Ile | Leu | Cys | Gly | Gln | Glu | Gln | Ala | Glu | Ala |
| | 195 | | | | | 200 | | | | | 205 | | | | |

| GGG | CCA | GGG | GTG | TGC | TCC | TTG | CTC | CTT | GCC | CAA | TCT | GAG | GTG | AAA | CCT | 798 |
| Gly | Pro | Gly | Val | Cys | Ser | Leu | Leu | Leu | Ala | Gln | Ser | Glu | Val | Lys | Pro |
| 210 | | | | | 215 | | | | | 220 | | | | | 225 |

| CAC | TGC | CTG | CTG | CTG | GTC | TTG | GCC | AAC | GGA | ACA | GAA | CTT | AGC | AGC | AAG | 846 |
| His | Cys | Leu | Leu | Leu | Val | Leu | Ala | Asn | Gly | Thr | Glu | Leu | Ser | Ser | Lys |
| | | | 230 | | | | | 235 | | | | | 240 | | |

| TTC | CTG | CTT | CTG | GAA | AAG | CAC | CAG | TCT | GAA | CTG | AGA | GAG | ATG | AGC | ATC | 894 |
| Phe | Leu | Leu | Leu | Glu | Lys | His | Gln | Ser | Glu | Leu | Arg | Glu | Met | Ser | Ile |
| | | 245 | | | | | 250 | | | | | 255 | | | |

| CAA | AAC | TTC | TCG | AAA | CAA | GAT | GTT | AGG | AGC | CAC | CAG | AGC | TAC | TCC | CGA | 942 |
| Gln | Asn | Phe | Ser | Lys | Gln | Asp | Val | Arg | Ser | His | Gln | Ser | Tyr | Ser | Arg |
| | | 260 | | | | | 265 | | | | | 270 | | | |

| AAG | ACC | TTG | ATT | GCA | CTG | GTC | ACC | TCG | GGG | ATC | CTG | CTG | GCT | GTC | TTG | 990 |
| Lys | Thr | Leu | Ile | Ala | Leu | Val | Thr | Ser | Gly | Ile | Leu | Leu | Ala | Val | Leu |
| | 275 | | | | | 280 | | | | | 285 | | | | |

| GGC | ATC | ACT | GGC | TAC | TTG | CTG | ATG | AAC | CGT | CGC | AGT | TGG | AGC | CCT | ACA | 1038 |
| Gly | Ile | Thr | Gly | Tyr | Leu | Leu | Met | Asn | Arg | Arg | Ser | Trp | Ser | Pro | Thr |
| 290 | | | | | 295 | | | | | 300 | | | | | 305 |

| GGA | GAA | AGG | CTG | GAG | CTG | GAA | CCC | TGA | | | | | | | | 1065 |
| Gly | Glu | Arg | Leu | Glu | Leu | Glu | Pro | | | | | | | | | |

(2) INFORMATION FOR SEQ ID NO: 19:

(i) SEQUENCE CHARACTERISTICS:
        (A) LENGTH: 344 AMINO ACIDS
        (B) TYPE: AMINO ACID
        (D) TOPOLOGY: LINEAR (iii) HYPOTHETICAL: NO (xi) SEQUENCE DESCRIPTION: SEQ ID NO: 19:

```
Met Leu Ile Arg Arg Gly Ala Arg Ala Gly Arg Gly Met Pro Arg Gly
    -30                 -25                 -20

Trp Thr Thr Leu Cys Leu Leu Ser Leu Leu Pro Ser Gly Phe Thr Ala
-15                 -10                  -5                    1

Val Asn Ser Ser Thr Ile Ala Ser Thr Leu Pro Ala Ala Gly Ser
                5                  10                  15

Thr Pro Thr Gly Pro Ala Thr Ala Gly Ala Ala Ile Thr Gly Ser Thr
            20                  25                  30

Ile Ser Asp Ile Ser Ser Pro Val Ser Thr Asn Ile Ser Asn Glu Glu
        35                  40                  45

Thr Thr Ser Asp Ala Phe Glu Ser Ala Ser Leu His Thr Val Ser Gln
50                  55                  60                  65

Gly Ser Ser Gly Thr Thr Val Ala Ile Ser Gly Pro Thr Val Asn Phe
                70                  75                  80

Met Ser Thr Ser Ala Val Thr Leu Val Pro Glu Thr Val Asn Ser Ser
            85                  90                  95

Val Gln Pro Gln Thr Ser Leu Ala Thr Ala Ser Ser Ala Thr Ile Asn
        100                 105                 110

Phe Thr Thr Ser Glu Val Thr Leu Gln Pro Ser Thr Phe Pro Gly Asn
115                 120                 125

Val Ser Asp Pro Leu Tyr Asn Ser Thr Ser Pro Ala Arg Ser Pro Thr
130                 135                 140                 145

Ser Pro Tyr Thr Ser Ser Pro Pro Thr Pro Gly Ser His Lys Gly Glu
            150                 155                 160

Val Lys Cys Ala Gln Ile Lys Glu Val Lys Leu Thr Gln Gly Ile Cys
        165                 170                 175

Leu Glu Arg Asn Glu Thr Ser Gly Cys Glu Lys Phe Lys Lys Asp Asn
        180                 185                 190

Gly Glu Lys Leu Met Gln Ile Leu Cys Gly Gln Glu Gln Ala Glu Ala
        195                 200                 205

Gly Pro Gly Val Cys Ser Leu Leu Leu Ala Gln Ser Glu Val Lys Pro
210                 215                 220                 225

His Cys Leu Leu Leu Val Leu Ala Asn Gly Thr Glu Leu Ser Ser Lys
            230                 235                 240

Phe Leu Leu Leu Glu Lys His Gln Ser Glu Leu Arg Glu Met Ser Ile
            245                 250                 255

Gln Asn Phe Ser Lys Gln Asp Val Arg Ser His Gln Ser Tyr Ser Arg
        260                 265                 270

Lys Thr Leu Ile Ala Leu Val Thr Ser Gly Ile Leu Leu Ala Val Leu
275                 280                 285

Gly Ile Thr Gly Tyr Leu Leu Met Asn Arg Arg Ser Trp Ser Pro Thr
290                 295                 300                 305

Gly Glu Arg Leu Glu Leu Glu Pro
            310
```

(2) INFORMATION FOR SEQ ID NO: 20:

(i) SEQUENCE CHARACTERISTICS:
        (A) LENGTH: 48 NUCLEOTIDES
        (B) TYPE: NUCLEIC ACID
        (C) STRANDEDNESS: SINGLE
        (D) TOPOLOGY: LINEAR (iii) HYPOTHETICAL: YES (iv) ANTI-SENSE: NO (xi) SEQUENCE DESCRIPTION: SEQ ID NO: 20:

TGTCTACTCG AGAAAAGAGA GGCTGAAGCT GTGAACAGCT CAACTATT    48

(2) INFORMATION FOR SEQ ID NO: 21:

(i) SEQUENCE CHARACTERISTICS:
        (A) LENGTH: 7 AMINO ACIDS
        (B) TYPE: AMINO ACID
        (D) TOPOLOGY: LINEAR (iii) HYPOTHETICAL: NO (xi) SEQUENCE DESCRIPTION: SEQ ID NO: 21:

Glu Lys Arg Glu Ala Glu Ala
1              5

(2) INFORMATION FOR SEQ ID NO: 22:

(i) SEQUENCE CHARACTERISTICS:
        (A) LENGTH: 34 NUCLEOTIDES
        (B) TYPE: NUCLEIC ACID
        (C) STRANDEDNESS: SINGLE
        (D) TOPOLOGY: LINEAR (iii) HYPOTHETICAL: NO (iv) ANTI-SENSE: YES (xi) SEQUENCE DESCRIPTION: SEQ ID NO: 22:

ACTAGAATTC TTATCACTTT CGGGAGTAGC TCTG    34